United States Patent [19]
Kuriakose et al.

[11] Patent Number: 6,073,478
[45] Date of Patent: Jun. 13, 2000

[54] HYDROGEN SENSOR USING A SOLID HYDROGEN ION CONDUCTING ELECTROLYTE

[75] Inventors: Areekattuthazhayil K. Kuriakose, Nepean; Nicola Maffei, Ohawa, both of Canada

[73] Assignee: Her Majesty the Queen in right of Canada, as represented by the Minister of Natural Resources, Ottawa, Canada

[21] Appl. No.: 09/016,391

[22] Filed: Feb. 2, 1998

[51] Int. Cl.[7] ................................................. G01N 27/00
[52] U.S. Cl. ................................................. 73/23.4; 73/23.28
[58] Field of Search ................................. 73/23.2, 23.21, 73/23.28, 23.4

[56] References Cited

U.S. PATENT DOCUMENTS

| | | | |
|---|---|---|---|
| 4,143,316 | 3/1979 | Roy et al. | 73/23 |
| 4,636,294 | 1/1987 | Novack et al. | 204/432 |
| 4,724,191 | 2/1988 | Kuriakose et al. | |
| 4,839,020 | 6/1989 | Yamaguchi et al. | 204/432 |
| 5,100,781 | 3/1992 | Greenbaum | 73/106 |
| 5,403,746 | 4/1995 | Bentsen et al. | 73/23.21 |
| 5,453,172 | 9/1995 | Alberti et al. | 204/421 |

FOREIGN PATENT DOCUMENTS

| | | |
|---|---|---|
| 1078019 | of 1980 | Canada. |
| 94/28403 | of 1994 | WIPO. |

*Primary Examiner*—Max Noori
*Attorney, Agent, or Firm*—Robert A. Wilkes

[57] ABSTRACT

A reliable gaseous hydrogen detection and measuring device which is simple, easy to use, does not require any reference gas supply, and which can be of reasonably rugged construction. The device utilizes a disc comprising a solid state ceramic hydronium conductor of the general formula $Na(H_3O)Zr_2Si_xP_{(3-x)}O_{12}$ together with a silver based electrode system on one side, and a catalytic noble metal electrode, such as platinum, on the other. By measurement of the output voltage across the electrodes, both the presence, and the amount, of hydrogen in a gaseous system can be determined.

13 Claims, 4 Drawing Sheets

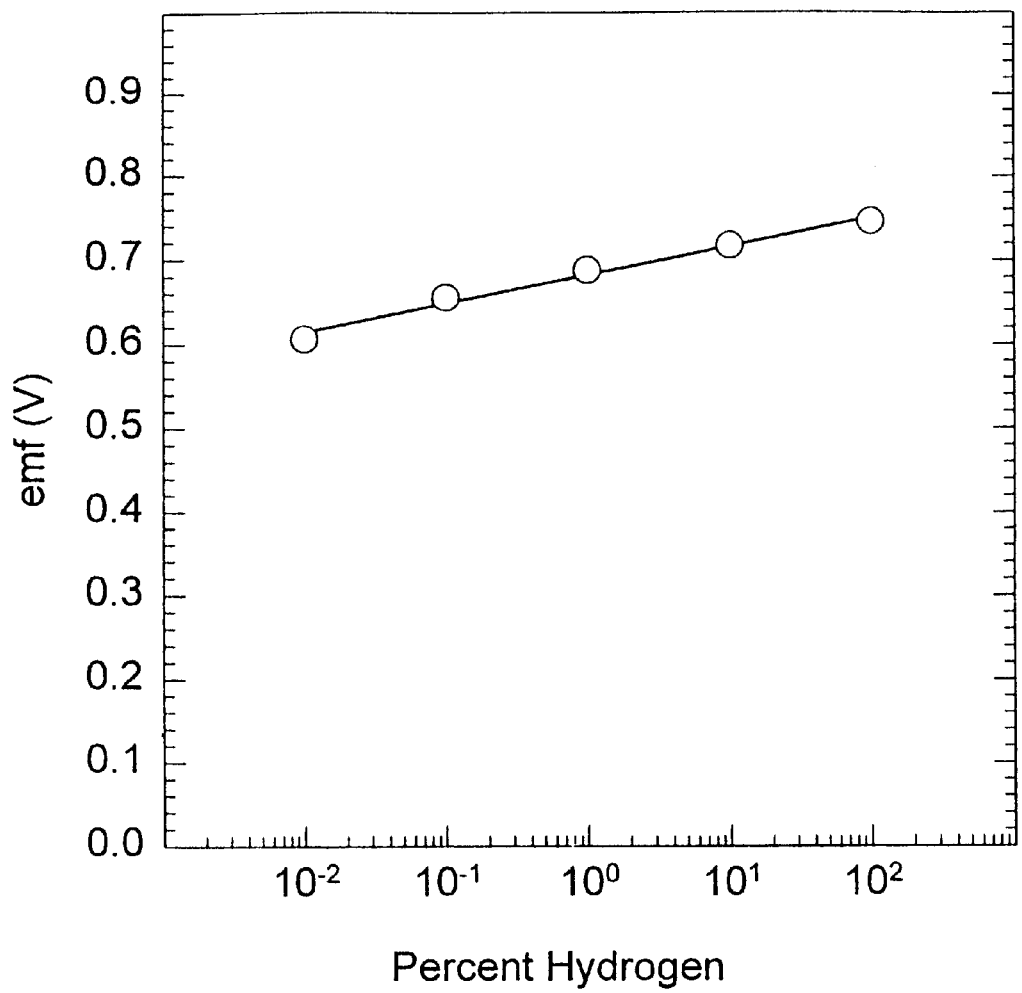
Figure 2. The voltage response of the sensor at various hydrogen concentrations in nitrogen

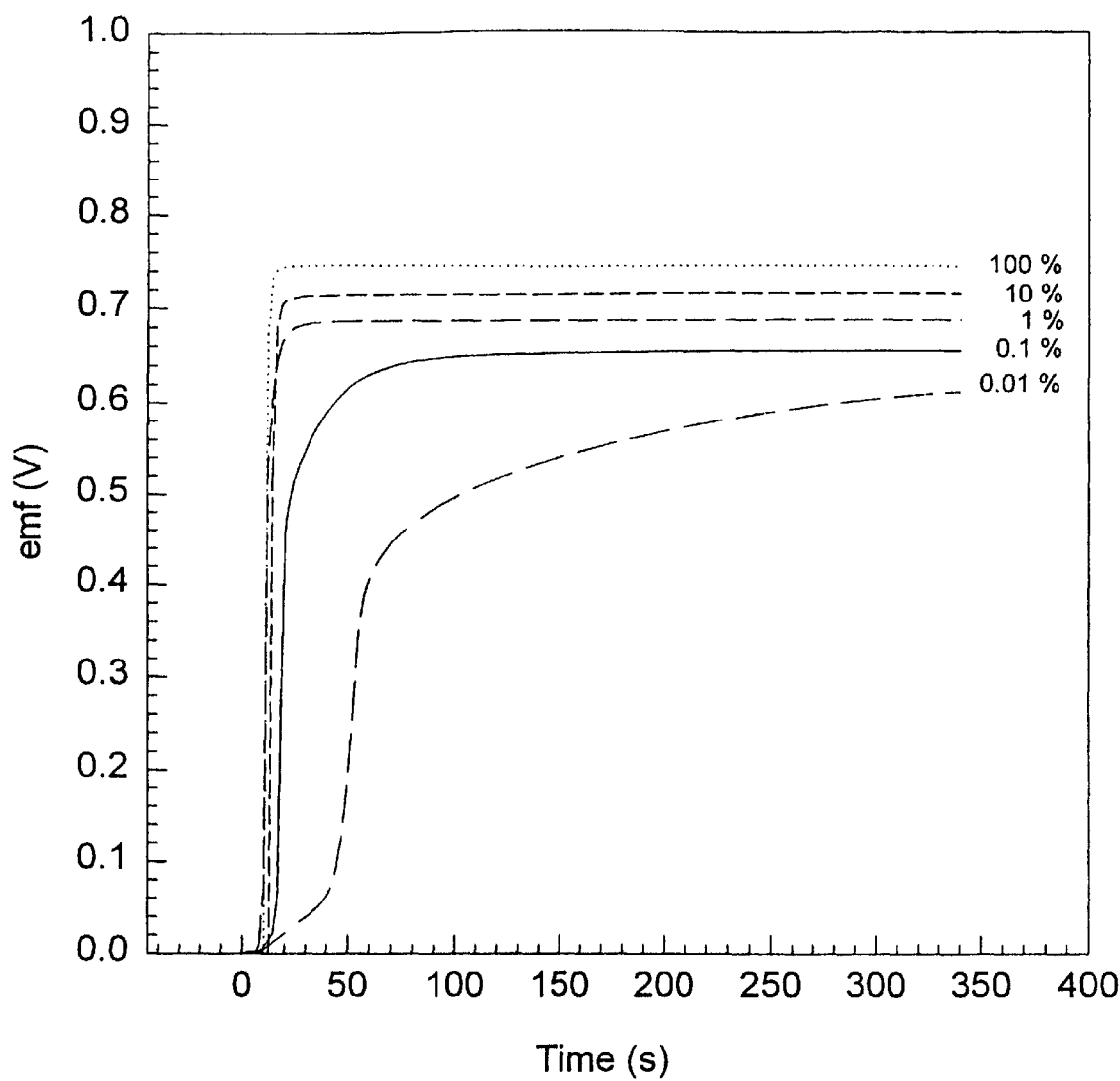
Figure 3. Response time of sensor to various hydrogen concentrations in nitrogen, after exposure to air.

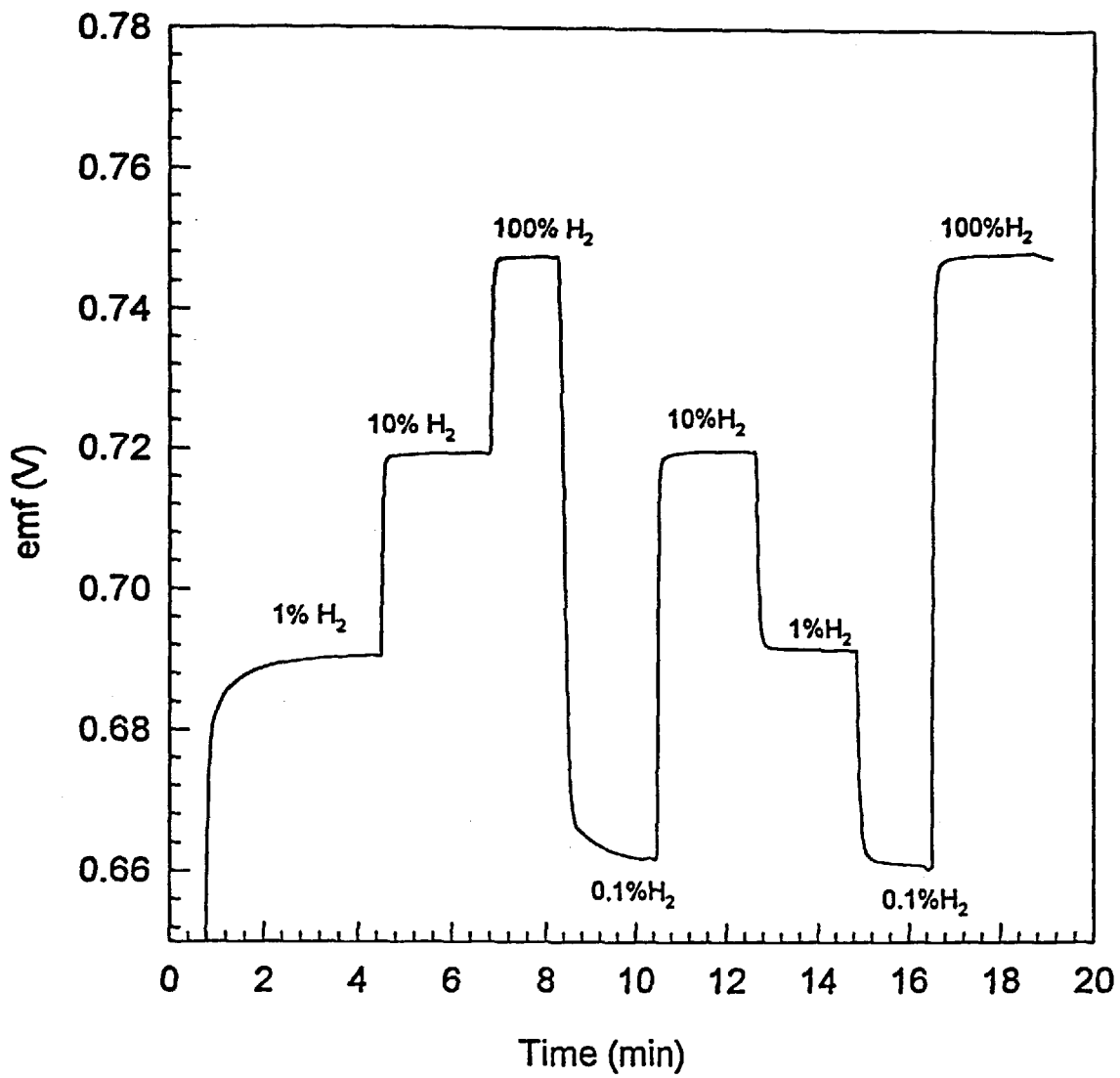
Fig. 4. The response time of the sensor to various hydrogen concentrations in nitrogen without exposure to air

HYDROGEN SENSOR USING A SOLID HYDROGEN ION CONDUCTING ELECTROLYTE

FIELD OF THE INVENTION

This invention is concerned with a hydrogen sensor including a solid hydrogen conducting electrolyte. Hydrogen sensors of this type are used to detect, and to measure, hydrogen when it is present in a gaseous system.

BACKGROUND OF THE INVENTION

Several types of hydrogen monitors and detectors have been described, which utilise a variety of principles related to the physicochemical properties of hydrogen. Some of these devices are only useful at low hydrogen concentrations, a typical upper limit being of the order of 3–4%. Others are able to operate over a wider, and more useful, range of concentrations, but generally either have low sensitivity and thus cannot detect small changes, or exhibit a slow response time and thus cannot respond to transient changes. Further, some of these devices require a supply of pure hydrogen as a standard reference, and some of them only operate at elevated temperatures.

It has also been proposed to use solid sensors in gas detection devices.

Ichinose et al., in CA 1,078,019, describe a gas detecting element including a gas detecting body made of a zinc oxide based semiconductor with a catalytic material coated onto its surface. This device measures the variation of the surface resistance of the semiconductor material when in contact with the gas. This device appears to be limited to detecting a combustible gas such as iso-butane, but also refers to hydrogen and carbon monoxide.

In U.S. Pat. No. 4,636,294 there is described a device for the detection and measurement of hydrogen sulphide. This device requires an anode, a cathode, a solid electrolyte, and a reference electrode in contact with the electrolyte. The reference electrode should be shielded from the gas being tested. It is also suggested that "sacrificial reference electrodes such as silver" can be used in such a device.

Alberti et al. in U.S. Pat. No. 5,453,172 describe a solid state gas sensor which comprises a solid protonic conductor sandwiched between a catalysing electrode on one side, and a solid state reference electrode on the other side. An end of the sandwich comprising these adjacent materials is exposed to the gas to be measured, and the emf generated across the outside layers of the sandwich is measured. This device is said to be suitable for hydrogen. The protonic conductor is preferably zirconium hydrogen phosphate, the catalysing electrode is preferably platinum or palladium, and the reference electrode is preferably titanium hydride or zirconium hydride. It is also indicated that there are drawbacks with using a silver electrode in contact with zirconium hydrogen phosphate which can lead to a total reduction of $Ag^+$ in such a system.

Currie et al. in WO 94/28403 describe an integrated monolithic gas sensor, which comprises a substrate carrying several deposited thin films. The thin films include an electrically conductive heating element, a conductive reference electrode, and a second conductive electrode. These three are electrically isolated from each other. A thin film ionic conductor, and a thin film reactive gas sensitive layer are placed between the reference electrode and the second conductive electrode to form an electrolytic cell in which an electrolyte reaction including as reagent the gas to be detected produces an emf between the two electrodes indicative of the concentration of the gas. The sensor also includes a micro thermometer formed of a deposited thin film wire having a temperature dependant resistance. When the gas to be detected is carbon dioxide, the reactive gas layer may be sodium carbonate, and the ionic conductor may comprise a complex zirconium phosphate of the Nasicon type, of general formula $Na_3Zr_2Si_2PO_{12}$.

A process for the preparation of polycrystalline ceramic materials which conduct electricity by the mobility of hydronium ions or hydrogen ions is described by Kuriakose et al in U.S. Pat. No. 4,724,191. This process includes methods for preparing both the so-called Nazirpos family of compounds, which are complex sodium zirconium silicophosphates corresponding to the general formula $Na_{(1+x)}Zr_2Si_xP_{(3-x)}O_{12}$, and other complex materials including polyantimonic acids, alumina containing ceramics, and complex sodium silicates of the general formula $Na_5ReSi_4O_{12}$, in which Re represents yttrium or gadolinium. Whilst it is stated that the polycrystalline materials obtained by the described process "are capable of use as a membrane in devices such as hydrogen fuel cells, hydrogen detectors, and steam electrolysers" no preference is expressed amongst the many ceramics that can be made by the described process, and further there is no disclosure of how a device capable of both detecting gaseous hydrogen, and measuring the amount of hydrogen present, can be constructed.

A hydrogen concentration cell in which an electrolyte from the Nazirpos family is used has been described (J. Can. Ceramic Soc., 55, 34–37 (1986), and Solid State Ionics, 45,299–310 (1991)). This cell was constructed by applying platinum paint to both sides of a disc of the ceramic, curing it in hydrogen at about 100° C., and sealing the disc onto the end of a glass tube with a silicone rubber resin. Electrical contact with the two platinised surfaces is stated to be obtained by means of a spring loaded platinum wire. This device functions as a concentration cell, in which one side (the side exposed within the glass tube) is exposed to hydrogen gas at a known partial pressure as a standard, and the other side of the cell is exposed to hydrogen gas either at a lower partial pressure, or in combination with another gas, for example nitrogen. Under these circumstances an emf is developed between the two electrodes indicative of the difference of the partial pressures of hydrogen at the two sides of the cell. This device has several disadvantages. It is difficult to ensure reliable electrical contact to the platinised ceramic surfaces with the spring loaded platinum contacts. The two sides of the ceramic disc have to be physically isolated from each other as different gas systems are in contact with each side of the cell. A reference gas of pure hydrogen at a known partial pressure also has to be provided.

BRIEF DESCRIPTION OF THE INVENTION

This invention seeks to provide a reliable hydrogen detection device which is simple, easy to use, and which does not require any reference gas supply. Further, the device can be of reasonably rugged construction, and thus is potentially suitable for commercial exploitation. This invention utilises a disc comprising a solid state ceramic hydronium conductor of the Nazirpos family together with a silver based electrode system on one side, and a platinum electrode on the other. The device can thus be represented as the following electrochemical cell:

$$Pt,H_2|H\text{-Nazirpsio}|Ag\text{-Nazirpsio}|Ag \qquad 1$$

In this cell the overall reaction is:

$$\tfrac{1}{2}H_2 + Ag\text{-Nazirpsio} \rightarrow Ag(s) + H\text{-Nazirpsio} \qquad 2$$

Thus in a first broad embodiment this invention seeks to provide a hydrogen detection device comprising in combination:

(a) a body of phosphate bonded ceramic electrolyte of the general formula $Na(H_3O)_xZr_2Si_xP_{(3-x)}O_{12}$ having a first face spaced apart from a second face;

(b) a catalytic noble metal electrode layer on the first face of the body in electrical contact with the ceramic electrolyte;

(c) a silver ion modified layer at the second face of the body;

(d) a silver electrode in contact with the silver ion modified layer; and (e) conductive leads electrically connected to each of the faces; whereby the emf generated when the ceramic body is exposed to hydrogen gas can be measured.

Preferably, the first and second spaced apart faces on the ceramic body are substantially parallel to each other.

Preferably, the first and second faces are each substantially flat.

Preferably, the ceramic body is disc shaped, and the first and second faces comprise the two faces of the disc.

Preferably, the catalytic noble metal electrode layer is chosen from a layer of platinum or palladium. More preferably, the catalytic noble metal electrode layer is a layer of platinum.

Preferably, the silver electrode comprises a silver containing conductive cement applied over the silver ion modified layer.

Preferably, the two conductive leads are attached to each of the platinum layer and the silver electrode by means of a conductive cement. More preferably, the same silver conducting cement is used as both the silver electrode and to attach the two conductive leads.

Preferably, in the body of phosphate bonded ceramic electrolyte of the general formula $Na(H_3O)_xZr_2Si_xP_{(3-x)}O_{12}$, x has a value of from about 1.3 to about 2.2.

Most preferably, in the body of ceramic electrolyte x has a value of about 1.5.

BRIEF DESCRIPTION OF THE DRAWINGS

One embodiment of the invention will now be described with reference to the drawings in which:

FIG. 2 shows graphically the voltage response of the device of FIG. 1 when exposed to hydrogen; and FIGS. 3 and 4 show the response time of the device of FIG. 1 to different concentrations of hydrogen under different conditions.

Figure 1:
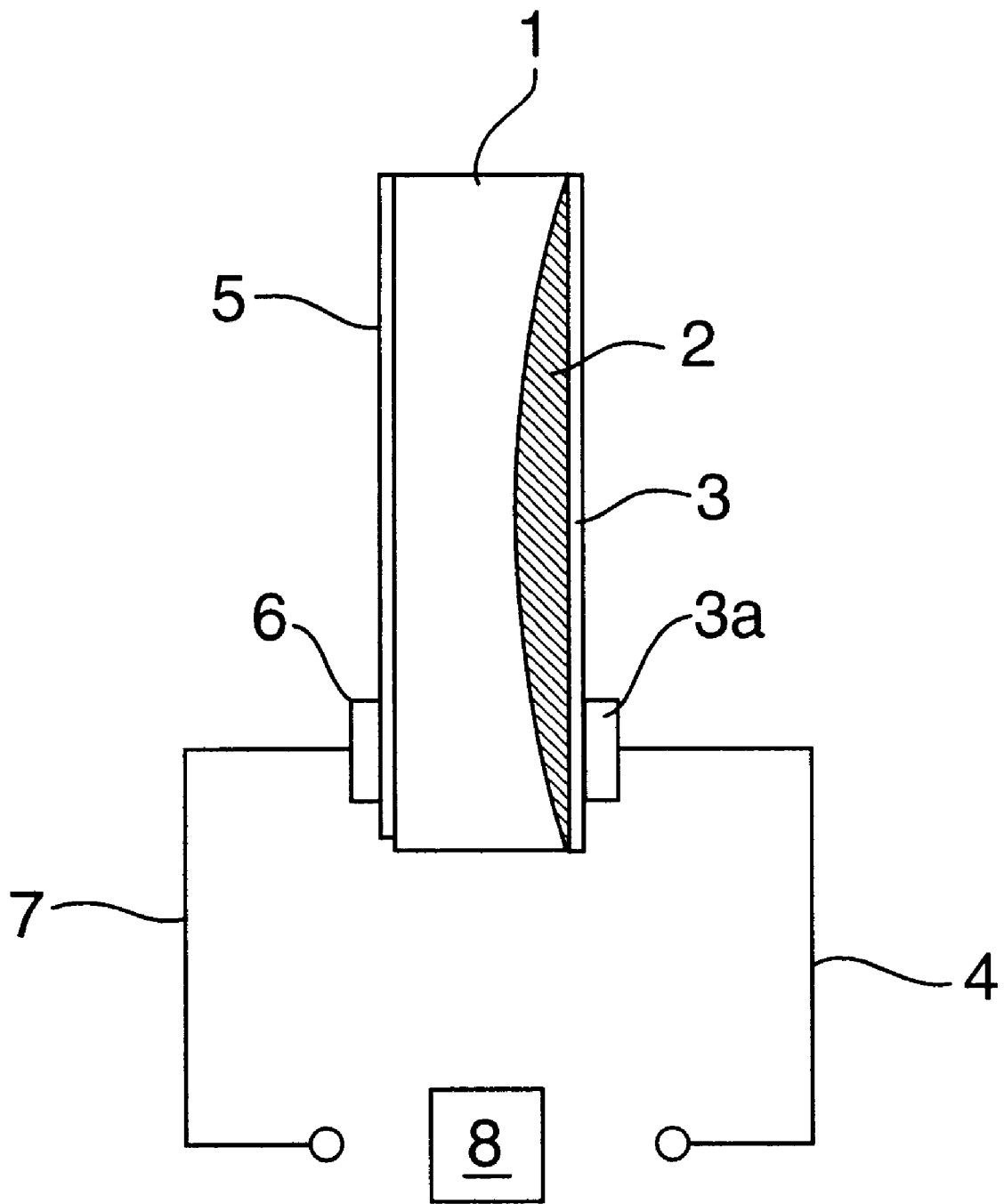
FIG. 1 shows a schematic diagram of a hydrogen detection device.

Referring first to FIG. 1, it can be seen that the construction of the device is not complex.

A substantially circular ceramic disc 1 having a composition chosen from the Nazirpos family is cut, and the two parallel faces a and b are ground flat, for example with 120 grit abrasive paper. The polished disc is cleaned in 2-propanol, and dried. To side a of the disc a 25% solution of silver nitrate in distilled water is applied as a thin layer. The disc is then allowed to stand for a suitable period of time, typically overnight, thus allowing the silver nitrate solution to diffuse into the surface of the disc. The silver nitrate also reacts with the ceramic to some extent to form the silver salts of the hydronium compounds in the ceramic, at and near to the surface of the disc, as indicated at 2. The area exposed to silver nitrate solution need not be all of the face of the disc, as shown in FIG. 1. The treated disc is then dried. This process can be represented by the following equation:

$$H\text{-Nazirpsio} + AgNO_3 \rightarrow Ag\text{-Nazirpsio} + HNO_3 \qquad 3$$

The nitric acid formed in this reaction is lost by evaporation from the surface of the disc.

The dry silver nitrate treated surface 2 is then coated with a layer of electrically conducting silver containing epoxy resin 3, and a silver wire 4 is attached to the layer 3 with the same silver containing epoxy resin 3a. The resin is then allowed to cure according to the manufacturer's instructions, typically at room temperature overnight.

After the epoxy resin is cured, the other side of the disc is coated with a platinum layer, as shown at 5, for example by applying a thin coating of platinum ink (available under the trade name Engelhard A-4338). After the ink has dried, a second silver wire 7 is attached to the layer 5 with a small amount 6 of the same silver containing epoxy resin, which leaves most of the platinised face open to contact the hydrogen containing gas. The resin layer 6 is then allowed to cure. As soon as the epoxy resin layers are cured, the device is ready for use.

The use of the silver containing epoxy resin in the construction of the device has two advantages. First, it removes the need to provide a separate silver electrode in contact with the silver ion modified layer in the surface of the ceramic disc. Second, it serves to provide a gas tight environment for the silver electrode, thus isolating the $Ag/Ag^+$ from the hydrogen containing gas, and providing what has been found to be a very steady and stable reference electrode system. As a separate benefit, if used on the platinum side as well the conductive cement helps to provide a rugged device suitable for industrial use. Other conductive cements can also be used, for example copper containing conductive epoxy resins are available, but it should be noted that it is then necessary to provide a separate silver electrode on the silver ion modified face of the ceramic.

The emf generated by the device is measured by a suitable measuring voltage means 8 connected between the silver wires 4 and 7. For this purpose any suitable high impedance voltage measuring device capable of measuring, and if desired recording in any suitable format, a voltage of around 1 volt DC can be used. Preferably, a voltage measuring device with an impedance of at least 10 megohms is used.

Using this procedure, a detector was constructed in which the disc was approximately 6 mm diameter by approximately 1 mm thickness. The phosphate bonded ceramic used was prepared as set out in U.S. Pat. No. 4,724,191, and had the formula $Na(H_3O)_xZr_2Si_xP_{(3-x)}O_{12}$, in which x was chosen to be 1.5. This device when exposed to hydrogen operates according to the reaction shown above as equation 2. Since the concentrations of all species other than hydrogen, as $H_2$, are substantially constant, the emf of this device may be represented by the following equation:

$$E = k + (RT/nF)\ln(PH_2)^{1/2} \qquad 4$$

in which:

E is the device output emf;

k is a constant;

R is the gas constant;

n is the number of electrons involved in the electrochemical process in Equation 1;

F is the Faraday number; and $PH_2$ is the partial pressure of hydrogen at the interface between the ceramic and the platinum layer coated onto it.

Elimination of the square root function, conversion to common logarithms, and substitution of the accepted values for R, T, n and F gives:

$$E = k + 0.02957 \log(PH_2) \text{ volts} \qquad 5,$$

in which 0.02957V is the Nernstian slope of the equation at 25° C. A plot of device output voltage against the logarithm of the hydrogen partial pressure yields a calibration curve for the device. A calibration curve for the device described above was obtained by measuring the device emf at about 25° C. when exposed to varying concentrations of hydrogen in nitrogen. The resulting calibration curve is shown in FIG. 2: the data is very close to the expected slope for this curve. It is noted that this calibration curve covers a wide range of hydrogen gas concentrations, from 0.01% up to 100%.

In U.S. Pat. No. 5,453,172 Alberti et al. indicate that there are drawbacks with using a silver electrode in contact with zirconium hydrogen phosphate which can lead to a total reduction of $Ag^+$ in such a system. Although the Nazirpsio ceramic used in this device is a complex phosphate bonded sodium hydronium zirconium silicophosphate, no difficulties of this nature have been encountered with the silver electrode used in conjunction with the silver ion containing modified layer in the ceramic in this device. It has also been found that if a silver electrode, for example the silver containing cement described above, is used without a silver ion containing modified layer in the surface of the Nazirpsio ceramic, a satisfactory reference electrode is not obtained and the device does not provide reliable or reproducible results.

For a hydrogen sensor to be useful, it is desirable that it react reasonably quickly to a change in hydrogen concentration. FIG. 3 demonstrates the speed with which the device described above responds to various concentrations of hydrogen in nitrogen, after the device had been exposed to air. For concentrations above about 1% the response time is of the order of 5 seconds or less to obtain a signal corresponding to about 90% of the final steady state value. At lower concentrations the response time increases. FIG. 4 demonstrates the speed with which the device described above responds to changes of hydrogen concentration without exposure to air in between the changes in hydrogen concentration. Again at concentrations above about 1% the response time is very short and is of the order of a few seconds and at lower concentrations the response time is somewhat longer.

It can thus be seen that this invention provides a simple and rugged hydrogen detection and measuring device. The device is capable of operating in contact with hydrogen concentrations or partial pressures ranging upwardly from quite low values to effectively 100%. Further, the device does not require an independent pure hydrogen gas supply for its reference electrode.

We claim:

1. A hydrogen detection device comprising in combination:
   (a) a body of phosphate bonded ceramic electrolyte of the general formula $Na(H_3O)_x Zr_2 Si_x P_{(3-x)} O_{12}$ having a first face spaced apart from a second face;
   (b) a layer of platinum on the first face of the body in electrical contact with the ceramic electrolyte;
   (c) a silver ion modified layer on and in the second face of the body;
   (d) a silver electrode in contact with the silver modified layer; and
   (e) conductive leads electrically connected to each of the faces;

whereby the emf generated when the ceramic body is exposed to hydrogen gas is measured.

2. A hydrogen detection device according to claim 1 wherein the first and second spaced apart faces on the ceramic body are substantially parallel to each other.

3. A hydrogen detection device according to claim 1 wherein the first and second faces are each substantially flat.

4. A hydrogen detection device according to claim 1 wherein the first and second spaced apart faces on the ceramic body are substantially parallel to each other, and wherein the first and second faces are each substantially flat.

5. A hydrogen detection device according to claim 4 wherein the ceramic body is disc shaped, and the first and second faces comprise the two faces of the disc.

6. A hydrogen detection device according to claim 1 wherein the silver electrode comprises a silver containing conductive cement applied over the silver ion modified layer.

7. A hydrogen detection device according to claim 1 wherein the two conductive leads are attached to each of the platinum layer and the silver electrode by means of a conductive cement.

8. A hydrogen detection device according to claim 1 wherein the same silver containing conducting cement is used as both the silver electrode and to attach the two conductive leads.

9. A hydrogen detection device according to claim 1 wherein the two conductive leads are both silver.

10. A hydrogen detection device according to claim 1 wherein in the body of ceramic electrolyte of the general formula $Na(H_3O)_x Zr_2 Si_x P_{(3-x)} O_{12}$, x has a value of from about 1.3 to about 2.2.

11. A hydrogen detection device according to claim 10 wherein x has a value of about 1.5.

12. A method of detecting hydrogen in a gaseous system which comprises exposing a detection device comprising in combination:
   (a) a body of phosphate bonded ceramic electrolyte of the general formula $Na(H_3O)_x Zr_2 Si_x P_{(3-x)} O_{12}$ having a first face spaced apart from a second face;
   (b) a layer of platinum on the first face of the body in electrical contact with the ceramic electrolyte;
   (c) a silver ion modified layer on and in the second face of the body;
   (d) a silver electrode in contact with the silver ion modified layer; and
   (e) conductive leads electrically connected to each of the faces;

to the gaseous system, and measuring the emf generated across the two conductive leads.

13. A method of measuring the concentration of hydrogen in a gaseous system which comprises:
   (i) exposing a detection device comprising in combination:
      (a) a body of ceramic electrolyte of the general formula $Na_{(1+x)} Zr_2 Si_x P_{(3-x)} O_{12}$ having a first face spaced apart from a second face;
      (b) a layer of platinum on the first face of the body in electrical contact with the ceramic electrolyte;
      (c) a silver ion modified layer on and in the second face of the body;

(d) a silver electrode in contact with the silver ion modified layer; and (e) conductive leads electrically connected to each of the faces;

to a plurality of gaseous systems each containing known amounts of hydrogen;

(ii) measuring the emf generated across the conductive leads by exposure to each gaseous system to provide a calibration curve for the device;

(iii) exposing the device to a gaseous system containing an unknown amount of hydrogen;

(iv) measuring the emf generated on exposure to gaseous system in step (iii); and (v) comparing the emf measured in step (iv) with the calibration curve obtained in step (ii).

* * * * *

UNITED STATES PATENT AND TRADEMARK OFFICE
CERTIFICATE OF CORRECTION

PATENT NO. : 6,073,478
DATED : June 13, 2000
INVENTOR(S) : Kuriakose et al.

It is certified that error appears in the above-identified patent and that said Letters Patent is hereby corrected as shown below:

Title page,
The address for inventor Maffei should read -- NEPEAN --

Signed and Sealed this

Sixth Day of November, 2001

*Attest:*

*Attesting Officer*

NICHOLAS P. GODICI
*Acting Director of the United States Patent and Trademark Office*